(12) United States Patent
Heath et al.

(10) Patent No.: US 7,806,690 B2
(45) Date of Patent: Oct. 5, 2010

(54) ENDODONTIC INSTRUMENT FOR PERFORMING ROOT CANAL THERAPY

(75) Inventors: Derek E. Heath, Vero Beach, FL (US); Steve Treadway, Johnson City, TN (US)

(73) Assignee: D&S Dental, LLC, Johnson City, TN (US)

( * ) Notice: Subject to any disclaimer, the term of this patent is extended or adjusted under 35 U.S.C. 154(b) by 158 days.

(21) Appl. No.: 12/044,699

(22) Filed: Mar. 7, 2008

(65) Prior Publication Data

US 2008/0220393 A1    Sep. 11, 2008

Related U.S. Application Data

(60) Provisional application No. 60/893,698, filed on Mar. 8, 2007.

(51) Int. Cl.
*A61C 5/02* (2006.01)

(52) U.S. Cl. ..................................................... 433/102

(58) Field of Classification Search .................. 433/81, 433/102, 224, 165
See application file for complete search history.

(56) References Cited

U.S. PATENT DOCUMENTS

| 4,330,278 | A | * | 5/1982 | Martin | ......................... 433/81 |
|---|---|---|---|---|---|
| 4,462,802 | A | | 7/1984 | Sekiya | |
| 5,429,502 | A | | 7/1995 | Cooper et al. | |
| 5,626,474 | A | | 5/1997 | Kukla et al. | |
| 5,695,513 | A | | 12/1997 | Johnson et al. | |
| 2003/0013067 | A1 | * | 1/2003 | Bleiweiss et al. | ........... 433/102 |
| 2004/0121283 | A1 | | 6/2004 | Mason | |
| 2006/0121405 | A1 | | 6/2006 | Hollard et al. | |

* cited by examiner

*Primary Examiner*—Cris L Rodriguez
*Assistant Examiner*—Heidi M Eide
(74) *Attorney, Agent, or Firm*—Luedeka, Neely & Graham, P.C.

(57) ABSTRACT

An endodontic instrument adapted for use in performing root canal therapy. The instrument includes a holder with a grip sized to be gripped by a hand of a user. An arm extends from the grip and has a length sufficient to permit a free end portion to reach into a patient's mouth while the grip remains outside the mouth. An elongate rod with a working portion having cutting portions thereon extends along the length of the arm of the holder such that a proximal end of the rod is adjacent the grip of the holder and the distal end of the rod with the working portion thereon extends from the free end portion of the arm, such that the working portion may be used to treat a root canal in a patient's mouth by a dentist manipulating the holder outside the mouth of the patient.

17 Claims, 3 Drawing Sheets

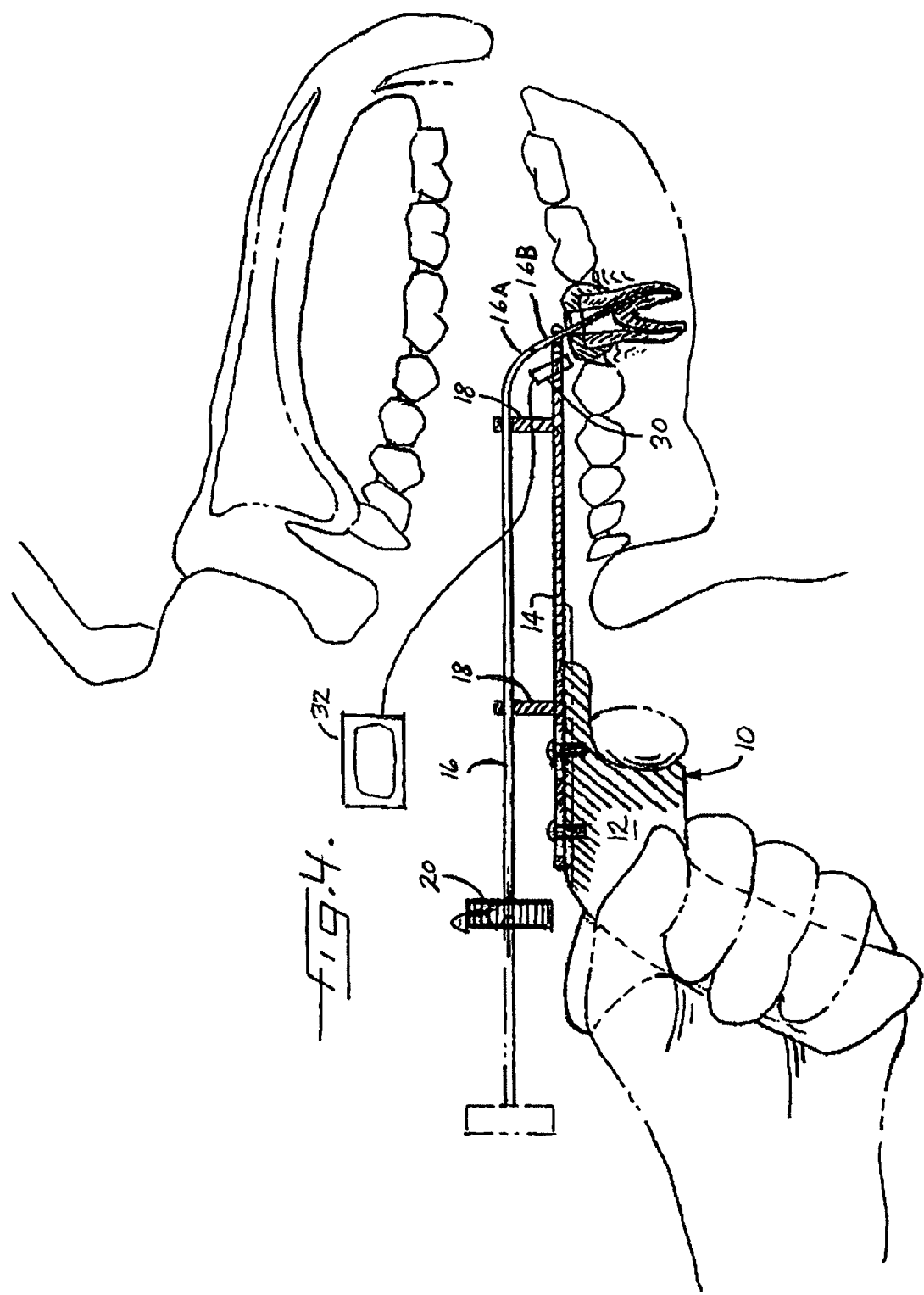

ENDODONTIC INSTRUMENT FOR PERFORMING ROOT CANAL THERAPY

CROSS REFERENCE TO RELATED APPLICATIONS

This application claims priority under 35 U.S.C. §119(e) to provisional application Ser. No. 60/893,698, filed Mar. 8, 2007.

BACKGROUND OF THE INVENTION

The present invention relates to an endodontic instrument adapted for use in performing root canal therapy on teeth.

Root canal therapy is a well-known procedure wherein the crown of a diseased tooth is opened so as to permit the canal to be cleaned and then filled. More particularly, as presently performed, a series of very delicate, flexible, finger-held instruments or files are used to clean out and shape the root canal, and each file is manually rotated and reciprocated in the canal by the dentist. Files of increasingly larger diameter are used in sequence, to achieve the desired cleaning and shaping. When the canal is thus prepared, it is solidly filled with a filling material, which typically comprises a waxy, rubbery compound known as gutta percha. In one procedure, the gutta percha is positioned on an instrument called a compactor, and the coated compactor is inserted into the prepared canal and rotated and reciprocated to compact the gutta percha therein. The dentist thereafter fills the tooth above the gutta percha with a protective cement, and lastly, a crown is fitted to the tooth.

Endodontic instruments of the described type were originally fabricated by permanently twisting a stainless steel rod of triangular or square cross section. The apices of the triangular or square cross section thus formed cutting edges which spiral along the length of the instrument. More recently, such instruments have been produced by a machining process, and wherein a cylindrical rod of stainless steel or nickel titanium alloy is cut into blanks of about two inches in length, and one end portion of each blank is tapered by machining the blank in a centerless grinding machine. Helical flutes are then machined on the tapered end portion, by moving the blank past a rotating grinding wheel and while the blank is slowly rotated to impart the desired helical configuration to the flutes. A cutting edge is thus formed along each side edge of each flute, and a helical land is preferably formed between the spiral flutes, as illustrated in U.S. Pat. No. 4,871,312 to Heath. A machining process as described above and which is particularly suitable for machining nickel titanium alloy is further described in U.S. Pat. Nos. 5,464,362 and 5,527,205 to Heath, et al., the disclosures of which are incorporated herein by reference.

Existing files of the described type typically comprise a shank which is composed of stainless steel or a nickel titanium alloy, and which has a length of about 30 mm (1.2 inches). The outer or proximate end of the shank mounts a conventional handle. The portion of the shank immediately below the handle is cylindrical and has a diameter of from about 0.5 and to about 1.6 mm (0.02 and 0.07 inches), and this shank portion includes calibrated depth markings of conventional design, note for example, U.S. Pat. No. 5,762,541 to Heath et al. The shank further includes an opposite distal or pilot end, and a working length is defined adjacent the pilot end. The working length may be cylindrical, or it may be slightly tapered toward the pilot end at an included angle of about one degree. The working length may have a length of about 2 mm (0.08 inches) up to the full length of the shank, i.e. about 30 mm (1.2 inches). In any event, the working length has a length sufficient to extend substantially the full depth of a tooth root canal, which typically is about 16 mm (0.63 inches).

In use, the dentist typically reaches into the mouth of the patient while gripping the handle of the instrument between two fingers. The pilot end of the shank is inserted in the root canal, and a repeating push-turn-pull motion is imparted to the instrument so that the cutting edges along the working length act to clean out and shape the root canal. During this procedure, the hand of the dentist visually obstructs the root canal, rendering it difficult to observe the calibration markings and thus the depth of penetration of the instrument into the canal.

It is accordingly an object of the present invention to provide an endodontic instrument which facilitates the viewing of the process within the mouth, by avoiding the need to insert the fingers of the dentist into the mouth of the patient.

It is a more particular object to provide an instrument of the described type which can be operated or manipulated by the dentist at a location outside of the mouth of the patient.

BRIEF SUMMARY OF THE INVENTION

The above and other objects and advantages of the invention are achieved by the provision of an endodontic instrument as described in the attached claims.

BRIEF DESCRIPTION OF THE DRAWINGS

Further advantages of the invention are apparent by reference to the detailed description in conjunction with the figures, wherein elements are not to scale so as to more clearly show the details, wherein like reference numbers indicate like elements throughout the several views, and wherein:

FIG. 4 is a partly schematic cross sectional view of an endodontic instrument with a sectional rod according to one embodiment of the present invention, shown positioned to operatively engage a root canal of one of the patient's teeth.

DETAILED DESCRIPTION OF THE INVENTION

The present inventions now will be described more fully hereinafter with reference to the accompanying drawings, in which a preferred, but not all embodiments of the invention is shown. Indeed, the invention may be embodied in many different forms and should not be construed as limited to the particular structure set forth herein; rather, the illustrated embodiment is provided so that this disclosure will satisfy applicable legal requirements. Like numbers refer to like elements throughout.

Figure 1:
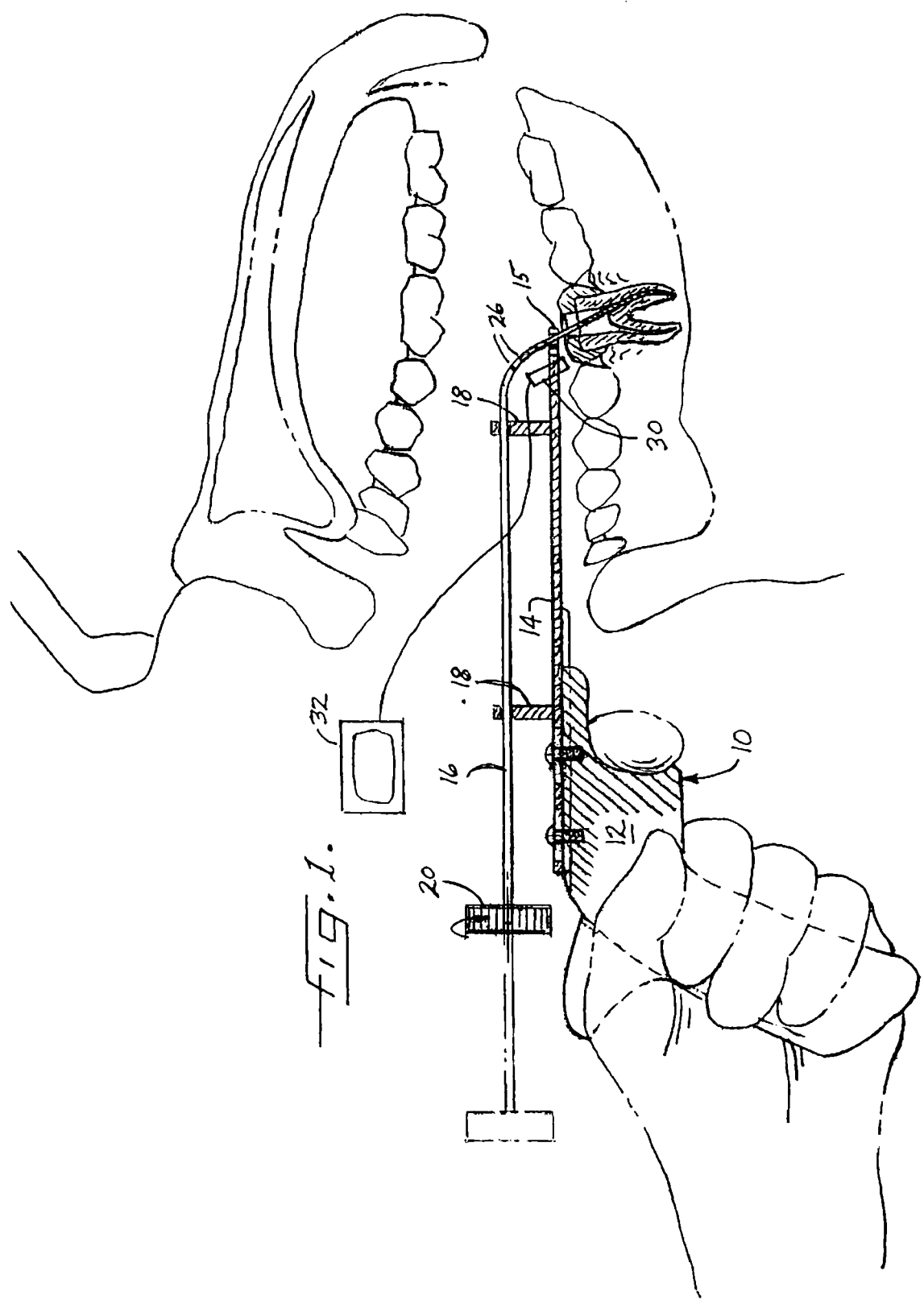
FIG. 1 is a partly schematic cross sectional view of an endodontic instrument which embodies the present invention, shown positioned to operatively engage a root canal of one of the patient's teeth.

Referring more particularly to the drawings, FIG. 1 illustrates an endodontic instrument in accordance with one embodiment of the present invention in a position of use. The instrument comprises a holder 10 which includes a grip 12 dimensioned to be gripped by one hand of the dentist. An elongate arm 14, preferably in the form of a flat metal plate, extends laterally from the grip for a preferred distance of about 6-8 inches. The arm 14 thus defines an interior end portion 15 remote from the grip and which can reach into a posterior portion of the mouth of a patient while the grip 12 remains outside the mouth.

The instrument further includes an elongate shank, preferably in the form of a cylindrical rod 16 of a nickel/titanium alloy or stainless steel, and having a diameter of from about 0.019 to about 0.062 inches, although the rod may have a larger diameter as needed to withstand peak or maximum torsional stresses expected to be imposed on the shank when using the instrument, and a length of from about 4 to about 9 inches. The rod 16 is preferably mounted to extend along the arm of the holder via a pair of posts 18 which are fixed to the arm. More particularly, the posts 18 include axially aligned apertures which closely receive the rod, and the apertures preferably include bushings of Teflon or the like to facilitate the axial movement and rotation of the rod 16 as described below while restricting radial movement of the same. In one alternate embodiment, a tubular sleeve is mounted in and extends between the aligned apertures in the posts 18 and the rod 16 is slidably and rotationally disposed within the tubular sleeve, which restricts radial movement of the same.

Figure 2:
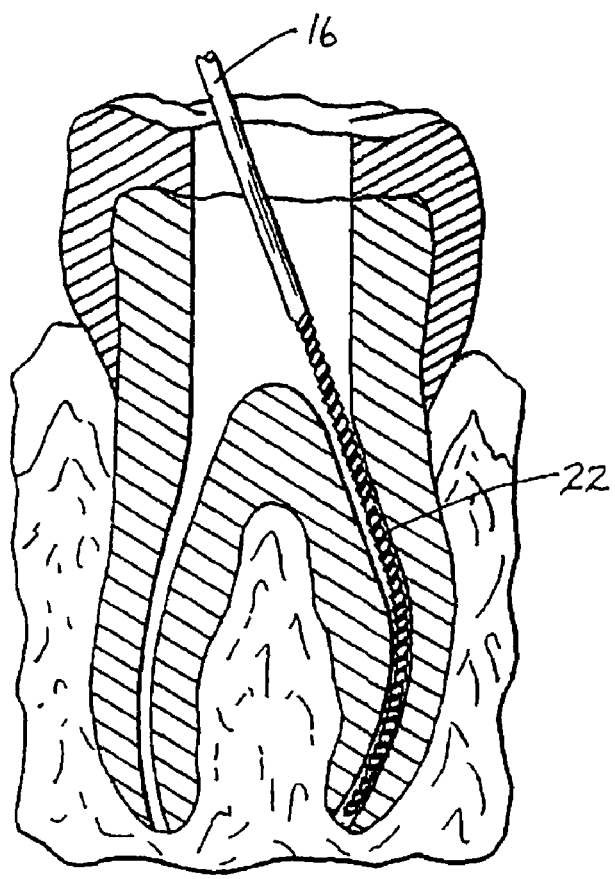
FIG. 2 is an enlarged view of the working length adjacent the pilot end of the instrument positioned in the root canal.
Figure 3:
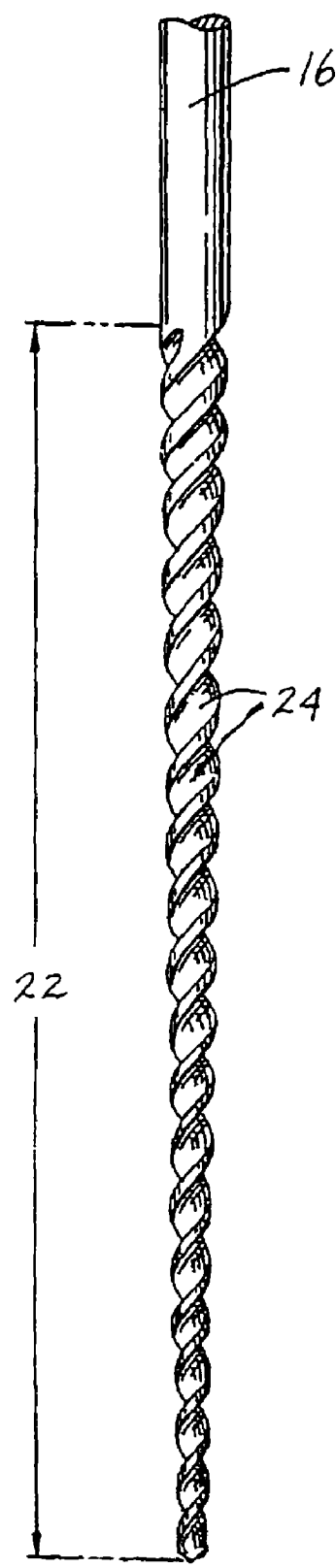
FIG. 3 is an enlarged side elevation view of the working length adjacent the pilot end of the instrument.

A proximate, rear, or exterior end of the rod 16 mounts a knob 20 dimensioned to be gripped in a facile manner by the free hand of the dentist, and the opposite pilot end portion of the rod defines a working length 22 (FIGS. 2-3). The knob preferably has a diameter larger than a typical handle of an endodontic instrument, which provides a dentist with greater sensitivity and tactile feedback, and also allows a dentist to place greater torque on the rod than would be easily obtainable with a typical manually manipulated instrument.

The working length 22 of the rod is preferably tapered and preferably extends from about 0.08 inches to about 1.2 inches, but may be longer as needed. The working length preferably includes at least one helical flute 24 having cutting side edges extending along its length, which is configured and formed as described for example in U.S. Pat. No. 5,106,298 to Heath et al. In alternate embodiments, the working length may be nontapered and/or may include non-helical radial cutting surfaces, barbed cutting surfaces, or other cutting surfaces known to those in the art.

The rod is preferably integral from the proximal end to the pilot end. However, in alternate embodiments, the rod may be sectional so that, for example, only a section of the rod including the working length may be changed when the instrument is used on multiple patients or the cutting surfaces on the working length become dull. For example, FIG. 4 shows a sectional rod with a first section 16A and a second section 16B including a replaceable working length.

The pilot end portion of the rod 16 is preferably curved so as to extend through a vertical aperture which extends through the interior end portion 15 of the arm and the aperture may also include a bushing of Teflon or the like. The pilot end portion of the rod thus extends in a direction which in use has a substantial vertical component.

The pilot end portion of the rod 16 also preferably includes calibration lines 26 to visually indicate the depth to which the working length is inserted into the root canal of the patient's tooth. Also, a stop pad (not shown) may be placed on the rod so as to engage one the posts 18 or the arm 14 and thereby limit the length of the rod which extends below the arm.

To improve the visibility of the operative area, the instrument may further include a micro camera 30 which is operatively connected to an external display monitor 32 to facilitate the viewing of the operative area by the dentist. Such camera systems are conventional and well known in the medical arts.

In use, the dentist positions the interior end portion 15 of the arm 14 within the patient's mouth, and positions the working length 22 of the rod 16 in the root canal of the tooth. The dentist then grips the knob 20 with his or her free hand, and while holding the holder steady, manipulates the knob so as to impart a repeating push-turn-pull motion, or other suitable motion, to the forward end portion of the rod. Note the dotted line position of the rod in FIG. 1 which illustrates its pulled back position. Alternatively, the rod 16 is sized to be frictionally engaged by the bushings in the apertures of the posts 18, and thus the grip 12 can be manipulated to achieve the desired repeating push-turn-pull motion to the rod. In either case, the procedure is performed with both hands of the dentist completely outside the patient's mouth, and the visibility of the operative area is thus enhanced.

The invention claimed is:

1. An endodontic instrument adapted for use in performing root canal therapy on a tooth, and comprising:
   a holder including a grip which is dimensioned to be gripped by a hand of a dentist, and an elongate arm which extends from the grip to a free end portion remote from the grip, with the arm having a length to permit the free end portion to reach into a posterior portion of a mouth of a patient while the grip remains outside the mouth,
   an elongate rod having a proximal end and an opposite pilot end and defining a working length substantially adjacent said pilot end, with at least one cutting surface on the working length, said rod being mounted to extend along at least a portion of the length of the arm of the holder so that the proximal end of the rod is adjacent the grip of the holder and a pilot end portion extends from an aperture in the free end portion of the arm of the holder,
   whereby the dentist can position the instrument so that the free end portion of the holder and the pilot end portion of the rod are positioned within a patient's mouth, with the grip and the proximal end of the rod located outside the mouth, and so that the pilot end of the rod can be advanced from outside a root canal substantially to an apex of the root canal by the dentist manipulating a first portion of the holder or the proximal end of the rod at a location outside the mouth of the patient without substantial movement of the grip.

2. The endodontic instrument as defined in claim 1 further comprising a camera attached to the holder so as to permit viewing of the pilot end of the shank displayed on an external video screen.

3. The endodontic instrument as defined in claim 1 wherein the rod is mounted to the arm of the holder so as be free to be axially reciprocated relative to the arm and rotated about its axis.

4. The endodontic instrument as defined in claim 3 further comprising a knob mounted to the proximal end of the rod to facilitate the axial reciprocation and rotation of the rod by the dentist.

5. The endodontic instrument as defined in claim 1 wherein the rod is slidably and rotationally disposed within a tubular sleeve mounted to the arm of the holder.

6. The endodontic instrument as defined in claim 1 wherein the rod comprises at least one helical cutting edge extending along the working length.

7. The endodontic instrument as defined in claim 1 wherein the rod is integral from its proximal end to the pilot end.

8. The endodontic instrument as defined in claim 1 wherein the rod comprises multiple sections such that a section including the working length may be easily removed and replaced.

9. The endodontic instrument as defined in claim 1 wherein the rod is mounted to the arm of the holder.

10. An endodontic instrument adapted for use in performing root canal therapy on a tooth, and comprising:
- a holder including a grip which is dimensioned to be gripped by a hand of a dentist, and an elongate arm which extends from a proximal end adjacent the grip to a distal end remote from the grip, with the arm having a length to permit the distal end of the arm to reach into a mouth of a patient while the grip remains outside the mouth,
- an elongate rod having a proximal end and an opposite pilot end and defining a working length adjacent said pilot end, with at least one cutting surface on the working length, a pilot end portion of the rod extending from an aperture in the arm adjacent the distal end of the arm of the holder,
- a knob mounted to the rod adjacent the rod's proximal end to facilitate axial reciprocation and rotation of the rod by the dentist,
- whereby the dentist can position the instrument so that the distal end of the arm and the pilot end portion of the rod are positioned within a patient's mouth, with the grip and the knob located outside the mouth, and so that the pilot end of the rod can be advanced into and out of a root canal by the dentist manipulating the knob at a location outside the mouth of the patient.

11. The endodontic instrument as defined in claim 10 further comprising a camera attached to the holder so as to permit viewing of the pilot end of the shank displayed on an external video screen.

12. The endodontic instrument as defined in claim 10 wherein the rod is mounted to the arm of the holder so as be free to be axially reciprocated relative to the arm and rotated about its axis.

13. The endodontic instrument as defined in claim 10 wherein the rod comprises at least one helical cutting edge extending along the working length.

14. An endodontic instrument adapted for use in performing root canal therapy on a tooth, and comprising
- a holder including a grip which is dimensioned to be gripped by a hand of a dentist, and an elongate arm which extends from a proximal end adjacent the grip to a distal end remote from the grip, with the arm having a length to permit the distal end of the arm to reach into a mouth of a patient while the grip remains outside the mouth,
- an elongate rod having a proximal end and an opposite pilot end and defining a working length adjacent said pilot end, with at least one cutting surface on the working length, a pilot end portion of the rod extending from an aperture in the arm adjacent the distal end of the arm of the holder,
- whereby the dentist can position the instrument so that the distal end of the arm and the pilot end portion of the rod are positioned within a patient's mouth, with the grip located outside the mouth, and so that the pilot end of the rod can be advanced into and out of a root canal by the dentist manipulating the proximal end of the rod from a location outside the mouth of the patient.

15. The endodontic instrument as defined in claim 14 wherein the rod is mounted to the arm of the holder so as be free to be axially reciprocated relative to the arm and rotated about its axis.

16. The endodontic instrument as defined in claim 14 wherein the rod is mounted to the arm of the holder.

17. The endodontic instrument as defined in claim 14 further comprising a camera attached to the holder so as to permit viewing of the pilot end of the shank displayed on an external video screen.

* * * * *